United States Patent [19]
Ohkoshi et al.

[11] Patent Number: 6,015,411
[45] Date of Patent: Jan. 18, 2000

[54] BONE EXCAVATING APPARATUS FOR REPAIRING LIGAMENT AND A BONE TUNNEL FORMING METHOD

[75] Inventors: Yasumitsu Ohkoshi, Hokkaido; Fumihito Naito, Aichi, both of Japan

[73] Assignee: Nagoya Screw Mfg. Co., Ltd., Nagoya, Japan

[21] Appl. No.: 09/030,423

[22] Filed: Feb. 25, 1998

[51] Int. Cl.[7] .................................................. A61B 17/16
[52] U.S. Cl. ................................ 606/80; 408/231; 279/93
[58] Field of Search ........................ 606/79, 80; 408/180, 408/223, 231, 713, 227, 229, 230; 279/93

[56] References Cited

U.S. PATENT DOCUMENTS

| | | | |
|---|---|---|---|
| 2,120,623 | 6/1938 | Oxford et al. | 279/1 |
| 2,379,984 | 7/1945 | Nereaux | 279/93 |
| 5,190,548 | 3/1993 | Davis | 606/80 |
| 5,320,115 | 6/1994 | Kenna | 128/898 |

*Primary Examiner*—Michael Buiz
*Assistant Examiner*—David O. Reip
*Attorney, Agent, or Firm*—Burns, Doane, Swecker & Mathis, LLP

[57] ABSTRACT

A bone-excavating apparatus comprises a shaft and a drill so sized as to be inserted into an articulation through a skin-cutting portion and removable from the shaft. In a state in which the shaft is installed on the drill, the shaft and the drill have a drill-locking mechanism for preventing the drill from being moved to a base side of the shaft and a torque transmission mechanism for transmitting, to the drill, a rotational force applied to the shaft in a direction in which a bone-excavating blade is allowed to excavate the bone.

14 Claims, 13 Drawing Sheets

6,015,411

BONE EXCAVATING APPARATUS FOR REPAIRING LIGAMENT AND A BONE TUNNEL FORMING METHOD

BACKGROUND OF THE INVENTION

The present invention relates to a bone tunnel forming method and a bone-excavating apparatus for repairing a ligament which is used to form a bone tunnel for introducing a repairing ligament which is to be transplanted thereinto in a ligament-repairing operation such as a posterior cruciate ligament-repairing operation.

In the posterior cruciate ligament-repairing operation, to implant a repairing ligament, for example, an artificial ligament on an articulation, a first bone hole is formed into the tibia and a second bone tunnel is formed into the femur. Then, the artificial ligament is implanted on the articulation by penetrating artificial ligament into the two bone tunnels. Thereafter, the ligament is fixed to a position proximately to an opening of the bone hole formed in the tibia and to an opening of the bone hole formed into the femur.

In this method, it is necessary to form the bone tunnel having almost the same inner diameter from the tibia side to the femur side. Thus, in carrying out an autotransplantation of a ligament, a large amount of a normal part of the tibia is taken out, which causes a large quantity of surgical invasion to be made on the normal part of the ligament. Further, a large amount of bone is lost in the articulation, which causes the bone to be weak. In addition, because it is necessary to cut off a large amount of bone, it takes much time and labor.

SUMMARY OF THE INVENTION

It is an object of the present invention to provide a bone-excavating apparatus, for repairing a ligament, forming a bone tunnel allowing the excavation amount of bone and the number of bone-removed portions to be small and allowing a ligament to be repaired by taking out a small amount of normal part therefrom.

In order to achieve the object, there is provided a bone-excavating apparatus for repairing a ligament comprises a rod-shaped shaft, and a drill having bone-excavating blade formed thereon such that the drill is insertable into an articulation from a cut portion thereof and removably installed on the shaft.

Further, in order to achieve the object, there is provided a bone tunnel forming method for a ligament-repairing operation comprises the steps of; forming a small bone hole extending from a tibia to a femur; forming a skin-cut portion at an articulation; inserting a drill of a bone-excavating apparatus into the articulation from the skin-cut portion; inserting a front end of a shaft of the bone-excavating apparatus into the articulation from an opening of the bone hole positioned at the tibia side; installing the drill on the front end of the shaft in such a manner that a blade of the drill faces a rear side of the shaft; rotating and pulling the shaft to excavate the bone by the drill and forming a bone tunnel of 10%–50% of the length of the small bone hole of the tibia; removing the shaft from the drill; taking out the drill from the articulation and drawing out the shaft from the small bone hole.

Further, in order to achieve the object, there is provided a bone tunnel forming method for a ligament-repairing operation comprises the steps of; forming a small bone hole extending from a tibia to a femur; forming a skin-cut portion at an articulation; inserting a drill of a bone-excavating apparatus into the articulation from the skin-cut portion; inserting a front end of a shaft of the bone-excavating apparatus into the articulation from an opening of the bone hole positioned at the femur side; installing the drill on the front end of the shaft in such a manner that a blade of the drill faces a front side of the shaft; rotating and pushing the shaft to excavate the bone by the drill and forming a bone tunnel of 10%–50% of the length of the small bone hole of the tibia; removing the shaft from the drill; taking out the drill from the articulation and drawing out the shaft from the small bone hole.

BRIEF DESCRIPTION OF THE DRAWINGS

Further objects, features and advantages of the present invention will become apparent from the following description of the preferred embodiments with reference to the accompanying drawings, wherein.

DESCRIPTION OF PREFERRED EMBODIMENTS

The bone-excavating apparatus for repairing a ligament (hereinafter referred to as bone-excavating apparatus) according to the embodiments of the present invention will be described below with reference to the drawings.

A bone-excavating apparatus 1 of the present invention comprises a shaft 2; and a drill 3 so sized as to be inserted into an articulation through a skin-cutting portion and installable on the shaft 2 and removable from the shaft 2. In a state in which the shaft 2 is installed on the drill 3, the shaft 2 and the drill 3 have a drill-locking mechanism for preventing the drill 3 from being moved to a rear side of the shaft 2; and a torque transmission mechanism for transmitting, to the drill 3, a rotational force applied to the shaft 2 in a direction in which a bone-excavating blade is allowed to excavate the bone. Further, in an embodiment which will be described later, there is provided a shaft removal prevention mechanism for allowing the engagement of the shaft 2 with the drill 3 when the shaft 2 is pulled toward the base side thereof, namely, toward an operator.

The present invention provides two types of bone-excavating apparatus. The first type bone-excavating apparatus is operated by rotating the shaft while it is being pulled to excavate the bone. The first type bone-excavating apparatus is hereinafter referred to as pulling/rotating type bone-excavating apparatus 1. The second type excavating apparatus is operated by rotating a shaft while it is being pushed to excavate the bone. The second type bone-excavating apparatus is hereinafter referred to as excavating pushing/rotating type apparatus 1.

A bone tunnel forming method for the ligament-repairing operation which is performed by using the bone-excavating apparatus of the two types will be described below with reference to FIGS. 27 through 30.

Initially, a bone tunnel at the tibia side is formed.

Figure 27:
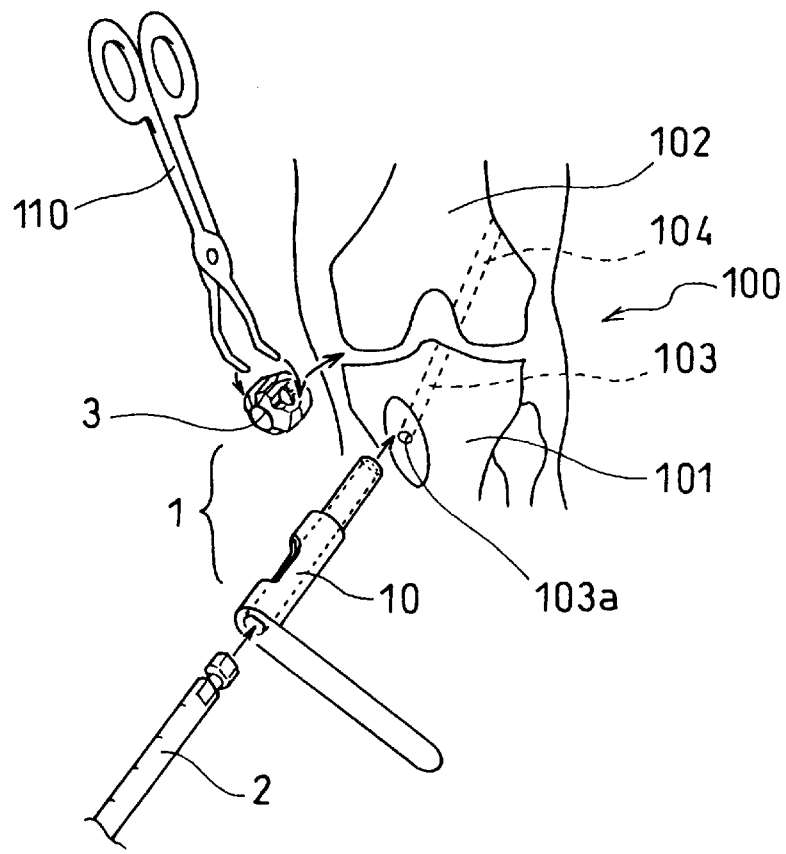
FIG. 27 is an explanatory view for explaining of a bone tunnel forming method according to the present invention using a pulling/rotating type bone-excavating apparatus.

In the operation of forming the bone tunnel, initially, an unshown guide pin is inserted into an upper portion on an aserine. Then, using the guide pin, an unshown cannulated drill is inserted through an articulation 100 from below the articulation 100 of the tibia 101 to form a small bone hole 103, whose inner diameter is 3–5 mm, extending to the femur, as shown in FIG. 27. In order to insert an arthroscope and forceps 110 into the articulation, a skin-cut portion is formed at a outer patella or the inner patella. Then, as shown in FIG. 27, the drill 3 of the pulling/rotating type held by the forceps 110 is inserted into the articulation from the skin-cut portion, using the arthroscope. Then, the front end of the shaft 2 of the bone-excavating apparatus 1 of pulling/rotating type is inserted into the articulation from an opening 103a of the bone hole 103 positioned at the tibia side.

Figure 10:
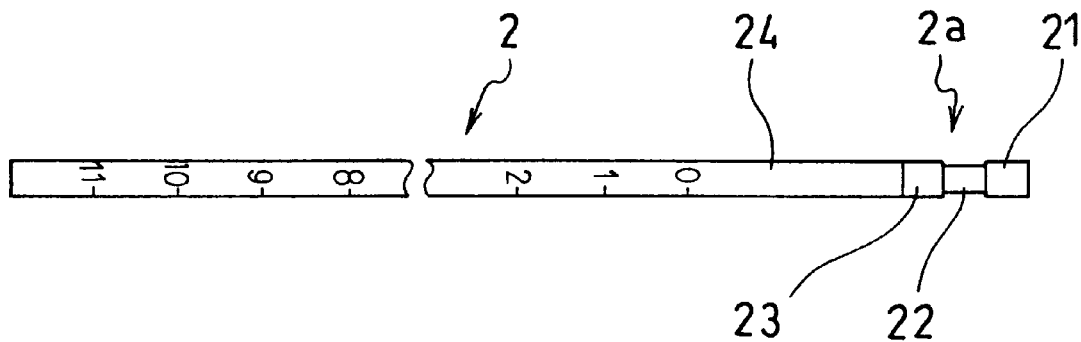
FIG. 10 is a partly abbreviated front view showing a shaft of the bone-excavating apparatus shown in FIG. 1.
Figure 11:
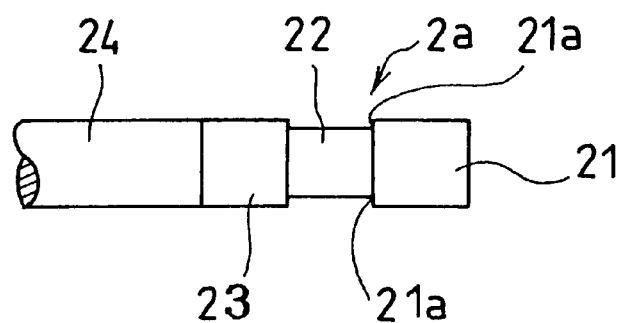
FIG. 11 is an enlarged front view showing the front end portion of the shaft shown in FIG. 10.
Figure 12:
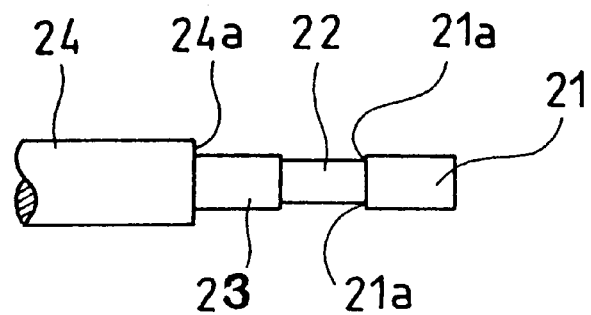
FIG. 12 is an enlarged front view showing the front end portion of the shaft shown in FIG. 10.

Using the arthroscope, the drill 3 is installed on the front end of the shaft 2 in such a manner that the blade of the drill 3 faces the base side of the shaft 2. Thereafter, the front end of the shaft 2 is inserted through a through-hole 35 of the drill 3. Then, the shaft 2 is rotated clockwise. As a result, the shaft 2 rotates about 45° with respect to the drill 3 to engage an engaging portion 23a (see FIGS. 10–12) formed at the front part of the shaft 2 with an engaging portion 36 (see FIGS. 5–8) formed at the rear part of the drill 3. Thus, when the shaft 2 is pulled toward the operator, namely, toward the base (rear) side of the shaft 2, the drill 3 is prevented from being removed from the shaft 2. When the shaft 2 is rotated clockwise in this state, the rotational force of the shaft 2 is transmitted to the drill 3. Consequently, the drill 3 rotates with the shaft 2, thus allowing the blade thereof to excavate the bone.

Figure 28:
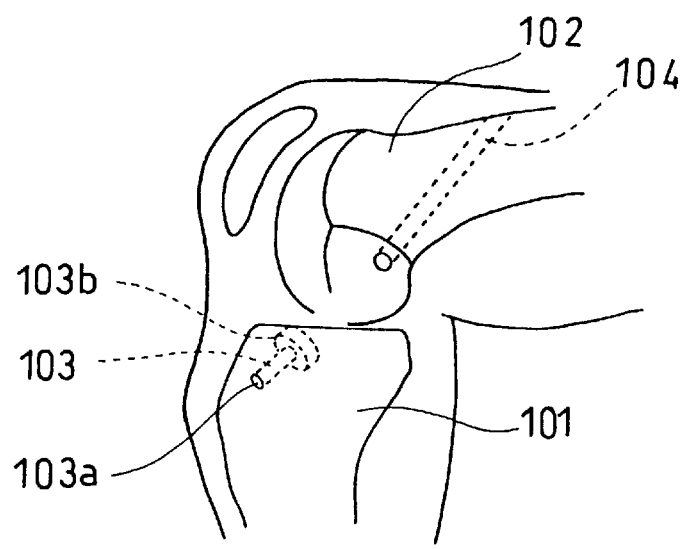
FIG. 28 is an explanatory view for explaining of a bone tunnel forming method according to the present invention using a pulling/rotating type bone-excavating.

In excavating the bone, a cylindrical sleeve 10 is installed on the shaft 2 from the base side thereof. The shaft 2 is rotated clockwise while it is being pulled by the right hand toward the base side thereof, with the cylindrical sleeve 10 gripped in the left hand to form the bone tunnel (wide bone hole 103b) on the tibia side along the shaft 2 (small hole 103). The length of the bone tunnel 103b is determined in advance by radiography, although it depends on the physical constitution and skeletal framework of a patient. Normally, the length of the bone tunnel is 10%–50%, preferably 20%–30%, of the length of the small bone hole 103 of the tibia. The bone tunnel having a necessary length is formed with reference to a calibration marked on the lateral of the shaft 2. After the formation of the bone tunnel at the tibia side is completed, the shaft 2 is rotated counterclockwise, with the drill 3 held with the forceps, using the arthroscope. As a result, the shaft 2 rotates about 45° relative to the drill 3, thus allowing the shaft side engaging portion 23a to be disengaged from the drill side engaging portion 36. Then, the shaft 2 is pulled toward the operator (to the base side of the shaft 2) to remove the shaft 2 from the drill 3. Then, the drill 3 2 are taken out from the articulation and the shaft 2 are drawn out from the small bone hole to terminate the formation of the bone tunnel at the tibia side, as shown in FIG. 28.

Thereafter, a bone tunnel at the femur side is formed.

Figure 29:
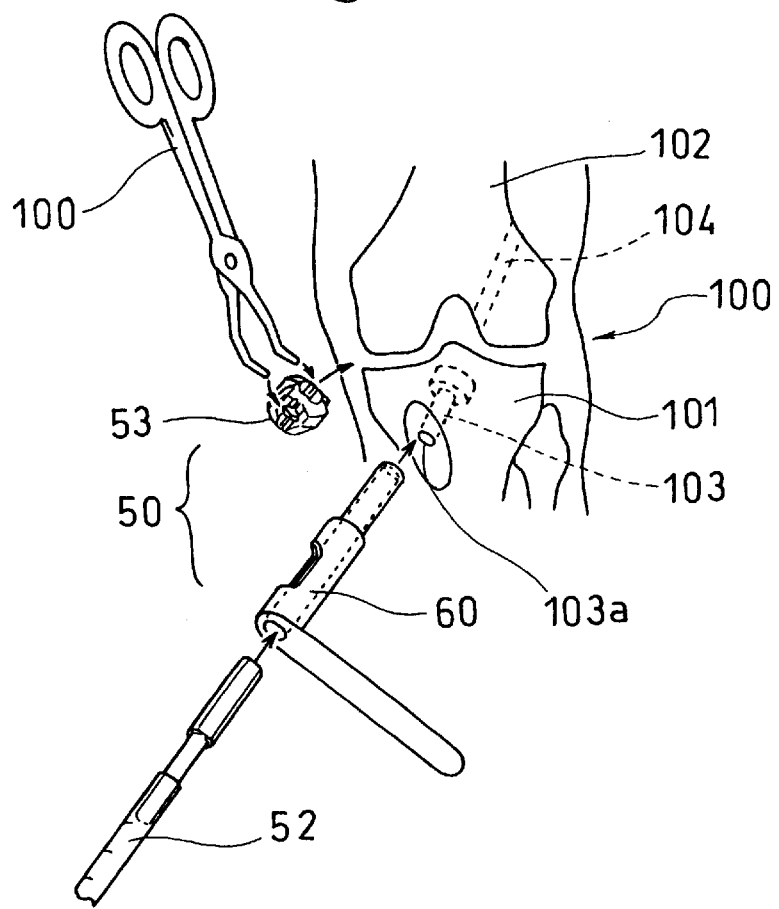
FIG. 29 is an explanatory view for explaining of a bone tunnel forming method according to the present invention using a pushing/rotating type.

As shown in FIG. 29, in order to insert the arthroscope and the forceps 110 into the articulation from the skin-cut portion previously formed. Then, the drill 53 of the pulling/rotating type held by the forceps 110 is inserted into the articulation, using the arthroscope. Then, the front end of the shaft 52 of the bone-excavating apparatus 50 of pushing/rotating type is inserted into the articulation from the opening 103a of the bone hole 103 positioned at the femur side.

Using the arthroscope, the drill 53 is installed on the front end of the shaft 52 in such a manner that the blade of the drill 53 faces the front side of the shaft 52. Then, the front end of the shaft 52 is inserted into a small bone hole 104. More specifically, the front end of the shaft 52 is inserted into a through-hole 65 of the drill 53 to install the drill 53 on the shaft 52. Then, the front end of the shaft 52 is moved into the small bone hole 104, with the shaft 52 in penetration through the drill 53. A portion, of the lateral of the drill 53, holding the drill 53 engages the inner surface of the drill 53. Thus, when the shaft 52 is rotated clockwise, the drill 53 rotates with the shaft 52, thus allowing the blade of the drill 53 to excavate the bone.

Figure 30:
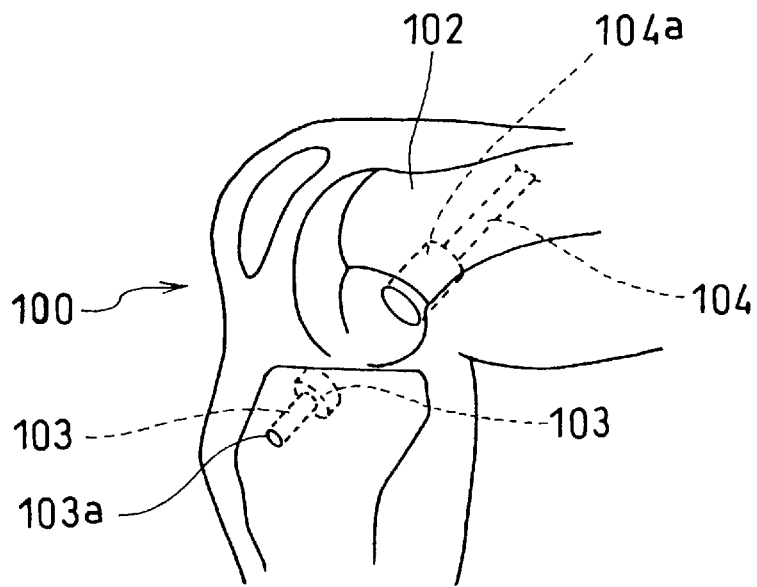
FIG. 30 is an explanatory view for explaining of a bone tunnel forming method according to the present invention using a pushing/rotating.

In excavating the bone, a cylindrical sleeve is installed on the shaft 52 from the base side thereof. The shaft 52 is rotated clockwise while it is being pushed by the right hand, with the cylindrical sleeve gripped in the left hand to form a bone tunnel on the femur side along the shaft 52 (small bone hole). The length of the bone tunnel is determined in advance by radiography, although it depends on the physical constitution and skeletal framework of a patient. Normally, the length of the bone tunnel is 10%–50%, preferably 20%–30%, of the length of the small hole of the femur. The bone tunnel having a necessary length is formed with reference to a calibration marked on the lateral of the shaft 52. After the formation of the bone tunnel at the femur side is completed, the shaft 52 is pulled toward the operator (to the base side of the shaft 52) to remove the shaft 52 from the drill 53. Then, the drill 53 are taken out from the articulation and the shaft 52 are drawn out from the small bone hole to terminate the formation of the bone tunnel at the tibia side, as shown in FIG. 30.

The method which is carried out by using the bone-excavating apparatus of the pulling/rotating type and that which is carried out by using the bone-excavating apparatus of the pushing/rotating type have been described. Although these methods facilitate the ligament-repairing operation, other method can be adopted.

For example, the bone tunnel at the femur side can be formed by using the bone-excavating apparatus of the pulling/rotating type. Similarly, the bone tunnel at the tibia side can be formed by using the bone-excavating apparatus of the pushing/rotating type.

More specifically, the drill of the bone-excavating apparatus of the pulling/rotating type held by the forceps is inserted into the articulation from the skin-cut portion, using the arthroscope. Then, the front end of the shaft of the bone-excavating apparatus of pulling/rotating type is inserted into the articulation from an opening of the bone hole positioned at the femur side. Using the arthroscope, the drill is installed on the front end of the shaft in such a manner that the blade of the drill faces the base side of the shaft. Thereafter, as described previously, the cylindrical sleeve is installed on the shaft from the base side thereof. The shaft is rotated clockwise while it is being pulled by the right hand toward the base side thereof, with the cylindrical sleeve gripped in the left hand to form the bone tunnel (bone hole) on the femur side along the shaft (small bone hole).

The drill of the bone-excavating apparatus of the pushing/rotating type held by the forceps is inserted into the articulation from the skin-cut portion, using the arthroscope. Then, the front end of the shaft of the bone-excavating apparatus of pulling/rotating type is inserted into the articulation from an opening of the bone hole positioned at the tibia side. Using the arthroscope, the drill is installed on the front end of the shaft in such a manner that the blade of the drill does not face the front side of the shaft. Thereafter, as described previously, the cylindrical sleeve is installed on the shaft from the base side thereof. The shaft is rotated clockwise while it is being pushed by the right hand, with the cylindrical sleeve gripped in the left hand to form the bone tunnel (bone hole) on the tibia side along the shaft (small bone hole).

Thus, it is possible to form the bone tunnel to repair the ligament without excavating a large amount of bone by using the bone-excavating apparatus of the pulling/rotating type or the bone-excavating apparatus of the pushing/rotating type.

The bone-excavating apparatus of the two types are described below more specifically.

Initially, the bone-excavating apparatus of the pulling/rotating type will be described below.

Figure 1:
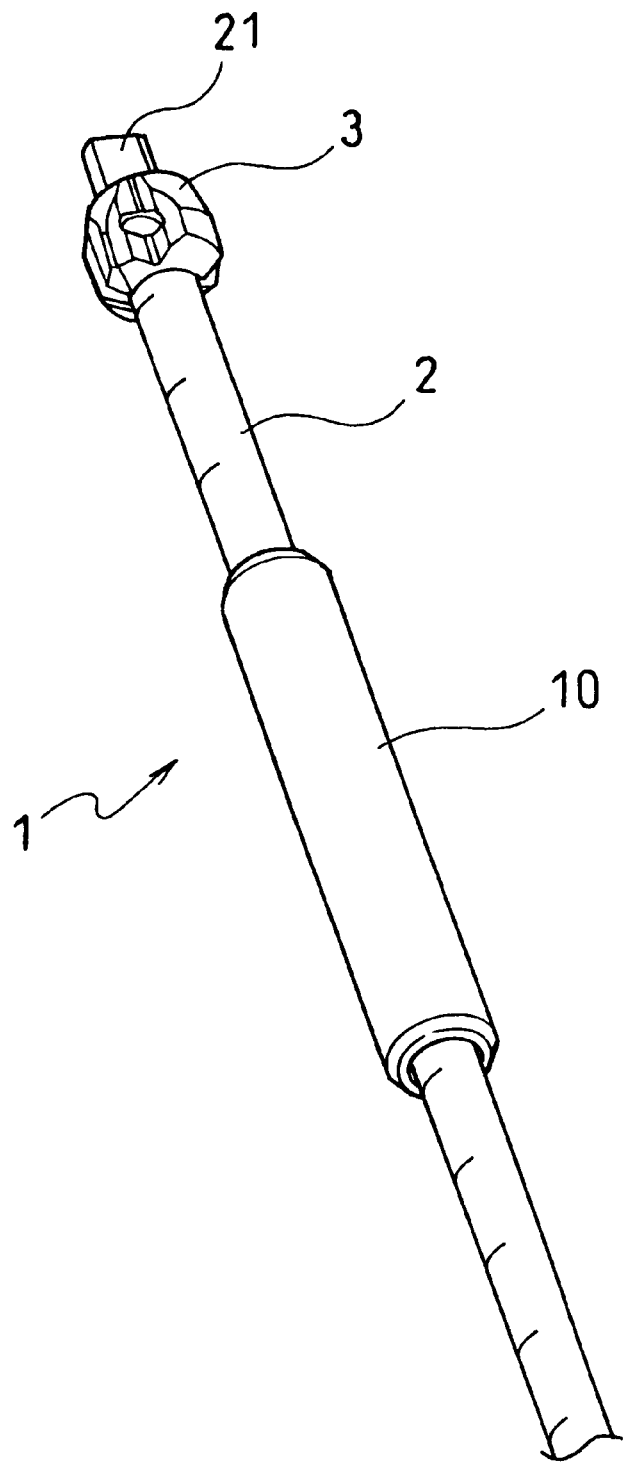
FIG. 1 is a perspective view showing the front part of a pulling/rotating type bone-excavating apparatus, for repairing a ligament, according to an embodiment of the present invention.
Figure 2:
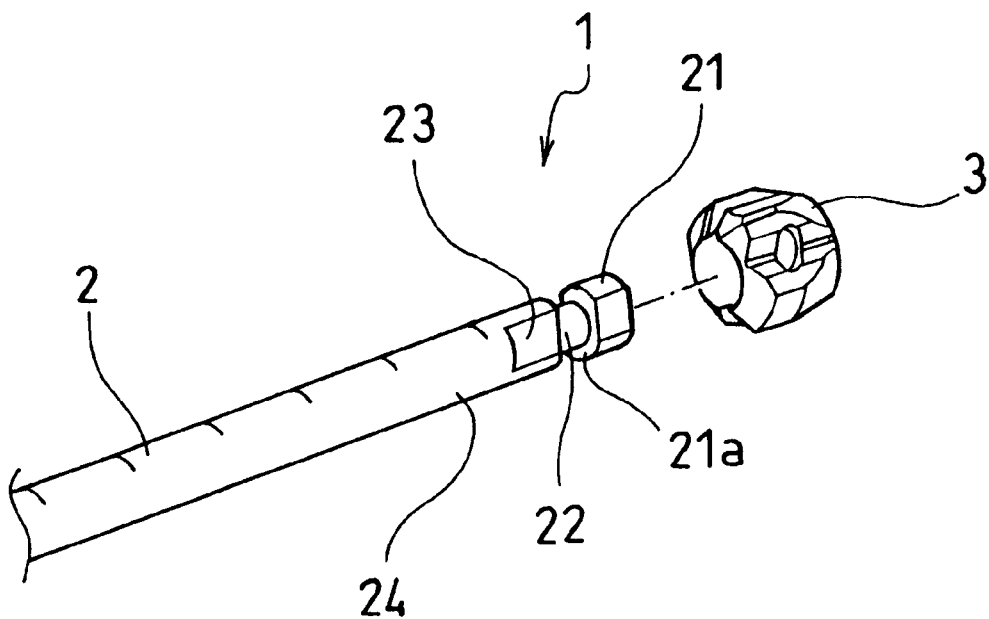
FIG. 2 is a perspective view showing a state in which a drill of the bone-excavating apparatus has been removed from a shaft thereof shown in FIG. 1.

As shown in FIGS. 1 and 2, the bone-excavating apparatus 1 comprises a shaft 2 and a drill 3 (pulling/rotating type drill) installably and removably installed on the shaft 2 at its front end.

The drill 3 is hollow. The shaft 2 is rotated clockwise while it is being pulled toward its base side to form a bone tunnel, with the drill 3 is installed to the shaft 2. The drill 3 is so sized as to be inserted into the articulation from a skin-cutting portion thereof. It is preferable to set the outer diameter of the drill 3 and the length thereof to 7–12 mm, respectively.

Figure 3:
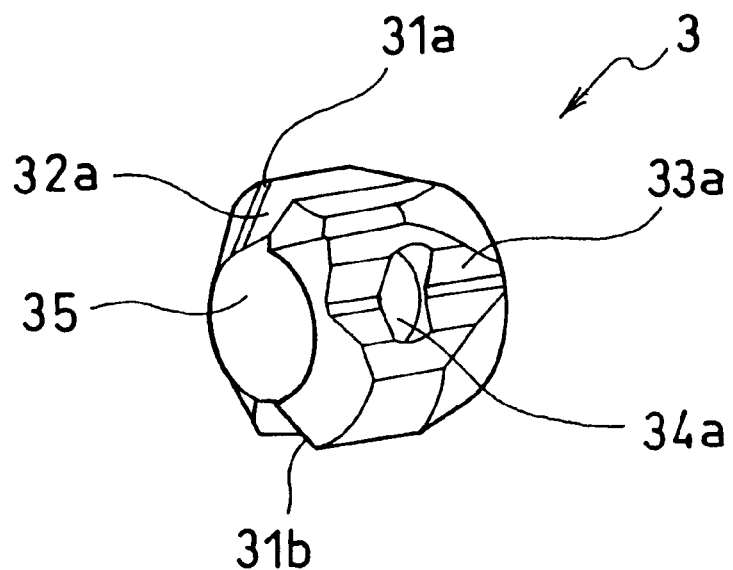
FIG. 3 is an enlarged perspective view showing the drill of the bone-excavating apparatus shown in FIG. 1.
Figure 4:
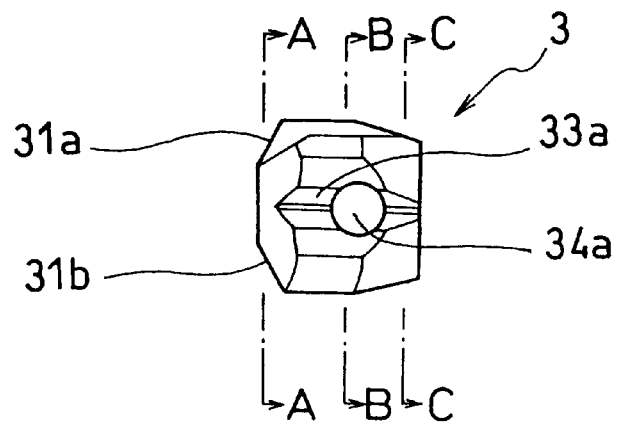
FIG. 4 is an enlarged front view showing the drill of the bone-excavating apparatus shown in FIG. 3.
Figure 5:
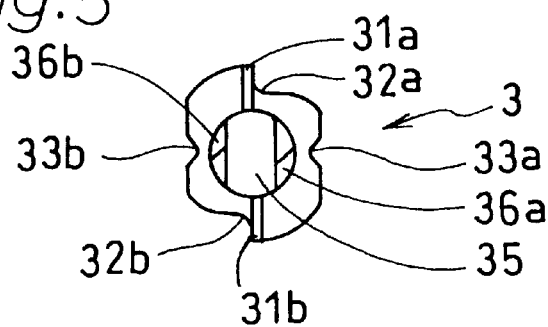
FIG. 5 is a left side elevation showing the drill of the bone-excavating apparatus shown in FIG. 4.

Referring to FIGS. 3, 4, and 5, the drill 3 comprises blades 31*a* and 31*b* formed on only the rear end surface thereof to prevent the skin and a normal part of the ligament from being injured; cut dust discharging grooves 32*a* and 32*b* continuous with each of the blades 31*a* and 31*b* and extending axially on the lateral thereof. The drill 3 has two V-shaped holding grooves 33 (33*a* and 33*b*) formed on the lateral thereof and facing each other to prevent the drill 3 from being shaken by a gripping means such as a forceps when it is inserted into the articulation. The V-shaped holding grooves 33*a* and 33*b* extend axially and are parallel with each other. The drill 3 has concavities 34*a* and 34*b* formed on the lateral thereof and facing each other. The concavities 34*a* and 34*b* are formed on each of the V-shaped holding grooves 33*a* and 33*b* to prevent the drill 3 from dropping from the gripping means such as the forceps.

The front peripheral part of the drill 3 is tapered to form a tapered portion thereon so that the drill 3 can be inserted easily into the articulation. The corner at which the tapered portion and the front part of the drill 3 intersect with each other is rounded to prevent the corner from being brought into contact with the skin or the like.

Figure 6:
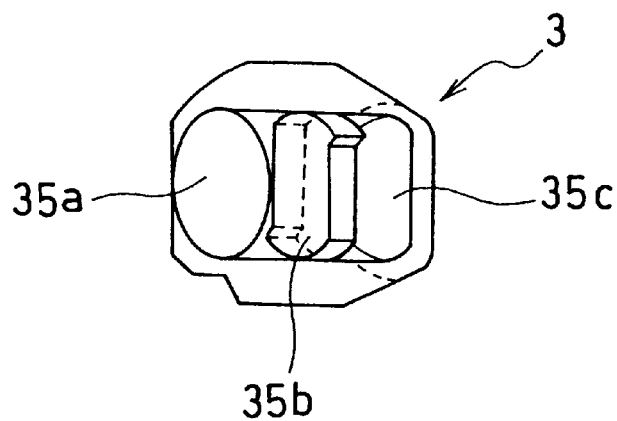
FIG. 6 is an explanatory view showing the inner shape of the drill of the bone-excavating apparatus shown in FIG. 3.
Figure 7:
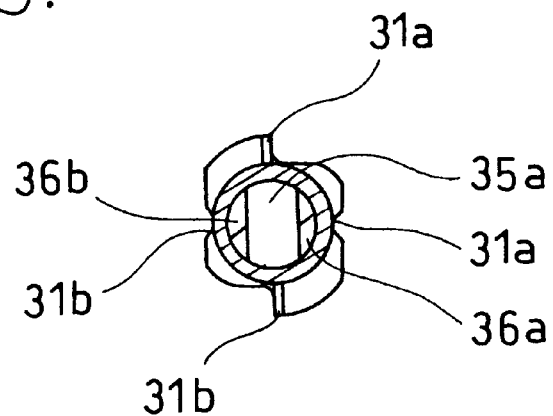
FIG. 7 is a sectional view taken along a line A—A of FIG. 4.
Figure 8:
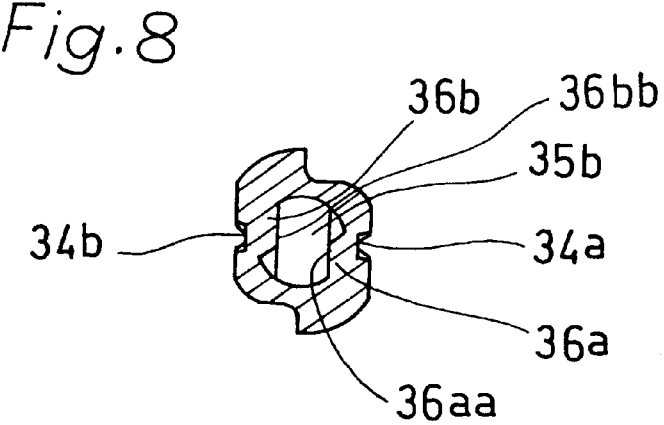
FIG. 8 is a sectional view taken along a line B—B of FIG. 4.
Figure 9:
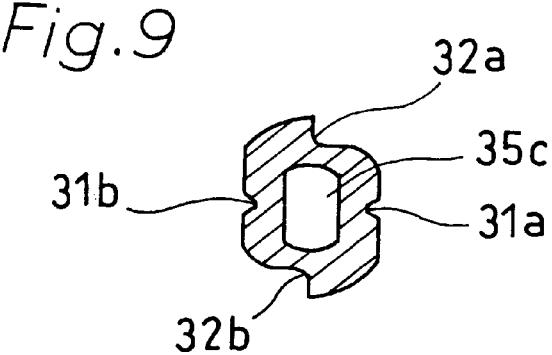
FIG. 9 is a sectional view taken along a line C—C of FIG. 4.
Figure 13:
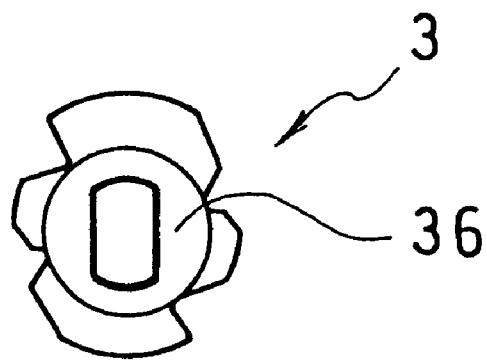
FIG. 13 is a side elevation showing the bone-excavating apparatus of the pulling/rotating type of the present invention in a state in which the shaft has been inserted into the drill.

A shaft-inserting through-hole 35 is axially formed inside the drill 3. As shown in FIGS. 6 and 7, the through-hole 35 of the drill 3 comprises parts 35*a*, 35*b*, and 35*c*. More specifically, the part 35*a* is positioned forward from the end of the drill 3 at the blade side (rear end) thereof to ⅓ (portion shown by line A—A in FIG. 4) of the whole length of the drill 3. As shown in FIGS. 6 and 7, the inner surface of the part 35*a* (the inner surface of the drill 3 is sectionally circular) is cylindrical. As shown in FIGS. 6 and 8, the part 35*b* is positioned forward from the part 35*a* in the range of ⅓ to ⅔ (portion shown by line B—B in FIG. 4) of the whole length of the drill 3. The part 35*b* has projections 36*a* and 36*b* which are parallel with each other and formed on a part of its cylindrical inner surface, i.e., the inner surface of the part 35*b* is sectionally deformed gourd-shaped. More specifically, the shape of the part 35*b* is formed by superimposing two similar or congruent quadrilaterals each having two parallel lines and two circular arcs on each other, with one quadrilateral rotated a predetermined angle (for example, 30–90°, 45° in the embodiment) on its center with respect to the other, after the centers of both quadrilaterals coincident with each other. The inner surface of the projection 36a and that of the projection 36b project inward in confrontation with each other in the through-hole 35, thus forming a small flat surfaces 36aa and 36bb, respectively extending in parallel with each other in the axial direction of the drill 3. As shown in FIGS. 7 and 8, the part 35c is positioned forward from the part 35b in the range from ⅔ to the front end (portion shown by line C—C in FIG. 4) of the whole length of the drill 3. The part 35c comprises two confronting flat surfaces and curved surfaces each continuous therewith. The two confronting flat surfaces are substantially parallel with each other and extend in the axial direction of the drill 3. As shown in FIG. 13, a part of the through-hole 35 positioned at the front end surface (blade-unprovided side) of the drill 3 is oval. That is, two parallel flat surfaces and circular arcs each continuous therewith are formed on the through-hole 35 at its front end.

Referring to FIGS. 2, 10, 11, and 12, the shaft 2 is inserted into the drill 3 from the front end part 2a. The front end part 2a comprises flat portion 21 formed on a cylinder; a small-diameter portion 22 positioned rearward from the first flat portion 21; a second flat portion 23 positioned rearward from the small-diameter portion 22; and a cylindrical portion 24 positioned rearward from the second flat portion 23. More specifically, the first flat portion 21 positioned at the front end of the shaft 2 has two flat surfaces extending substantially parallel with each other in the axial direction of the shaft 2. The small-diameter portion 22 consisting of a groove extending circumferentially is continuous with the first flat portion 21 and smaller in than the first flat portion 21 in diameter. The outer diameter or the maximum diameter of the small-diameter portion 22 is smaller than the shortest distance of the inner diameter of the part 35c of the drill 3. The second flat portion 23 continuous with the small-diameter portion 22 has two flat surfaces formed on a cylinder and extending in substantially parallel with each other in the axial direction of the shaft 2. The cylindrical portion 24 is continuous with the second flat portion 23. It is preferable that the outer diameter of the shaft 2 is 2–7 mm.

When the front end part 2a of the shaft 2 is inserted into the through-hole 35 of the drill 3, the first flat portion 21 at the front end part 2a of the shaft 2 penetrates through the through-hole 35, thus projecting forward from the front end of the drill 3, as shown in FIG. 13. As described above, the through-hole 35 comprises the part 35a, the part 35b, and the part 35c. The inner surface of the part 35a is cylindrical, namely, circular sectionally. The part 35b has the small parallel projections formed on its cylindrical surface. The inner surface of the part 35c is oval sectionally.

In this state, the small-diameter portion 22 of the shaft 2, the second flat portion 23 thereof, and the cylindrical portion 24 thereof are positioned in the part 35c of the through-hole 35 of the drill 3; the part 35b (intermediate between the part 35c and the part 35a) of the through-hole 35 having the parallel projections 36a and 36b of the drill 3; and the part 35a of the through-hole 35 of the drill 3, respectively. Because the rear end (blade-provided side) of the parallel projections 36a and 36b formed at the center part 35b of the through-hole 35 contact the end 24a (shown in FIG. 12) of the cylindrical portion 24, the drill 3 cannot be moved toward the base side of the shaft 2 beyond the end 24a. In the embodiment, a drill-locking mechanism is constituted of the rear end of the parallel projections 36a and 36b at the blade-provided side of the drill 3 and the end 24a of the cylindrical portion 24 of the shaft 2 to prevent the drill 3 from moving toward the base side of the shaft 2. Because the cylindrical portion 24 of the shaft 2 is positioned in the part 35a of the drill 3, there is no space left between the excavating surface of the drill 3 and the shaft 2. Thus, cut dust of the bone can be prevented from flowing into the space.

Because the drill 3 and the shaft 2 have the above-described construction, respectively, the shaft 2 does not rotate inside the drill 3 even though the operation of rotating the shaft 2 counterclockwise is performed. But when a force is applied to the shaft 2 clockwise, the shaft 2 rotates a predetermined small angle because of the relationship between the construction of the second flat portion 23 of the shaft 23 and that of the part 35b of the drill 3. More specifically, as described above, the shape of the part 35b is formed by superimposing two similar or congruent quadrilaterals each having two parallel lines and two circular arcs on each other, with one quadrilateral rotated a predetermined angle (for example, 30–90°, 45° in the embodiment) on its center with respect to the other, after the centers of both quadrilaterals coincident with each other. As a result, one of the flat surfaces of the second flat portion 23 contacts the flat surface of the projection 36a and that of the projection 36b. When a force is further applied clockwise to the shaft 2, the rotational force of the shaft 2 is transmitted to the drill 3. In the embodiment, a torque transmission mechanism for transmitting, to the drill 3, the rotational force generated by applying a force to the shaft 2 to allow the blade to excavate the bone is constituted of one of the flat surfaces of the second flat portion 23 and the flat surface of one of the projections 36a and 36b.

Figure 14:
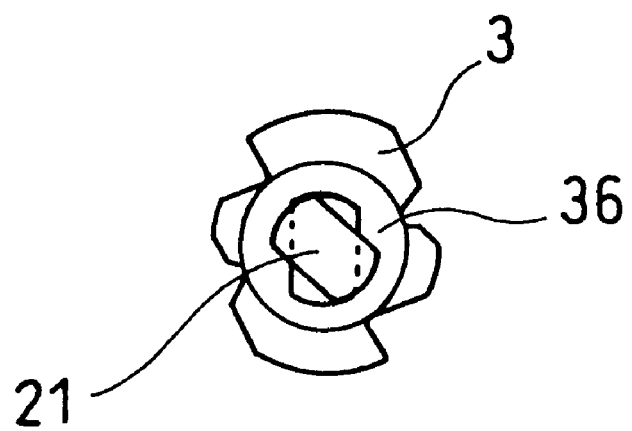
FIG. 14 is a side elevation showing the bone-excavating apparatus of the pulling/rotating type of the present invention in a state in which the shaft has engaged the drill.

As shown in FIG. 14, as a result of the rotation of the shaft 2 of the permissible range inside the drill 3, a part of a rear edge 21a (shaft side engaging portion) of the first flat portion 21 of the shaft 2 is coincident with the rear end surface 36 (drill side engaging portion) of the drill 3, with the rear edge 21a of the first flat portion 21 in contact with the rear end surface 36. When the shaft 2 is pulled toward the operator, both engage each other. Accordingly, the shaft 2 can be prevented from being removed from the drill 3, and a pulling force applied to the shaft 2 is transmitted to the drill 3. That is, in the embodiment, the rear edge 21a of the first flat portion 21 of the shaft 2 and the rear end surface 36 of the drill 3 constitute a shaft removal prevention mechanism for engaging the shaft 2 with the drill 3 and a pulling force transmission mechanism operating when the shaft 2 is pulled toward the base side thereof. Thus, the bone can be excavated by rotating the shaft 2 clockwise while it is being pulled.

When the shaft 2 is rotated counterclockwise, the rear edge 21a (shaft side engaging portion) of the first flat portion 21 of the shaft 2 and the rear end surface 36 (drill side engaging portion) of the drill 3 disengage from each other. Thus, the shaft 2 can be removed from the drill 3.

Figure 15:
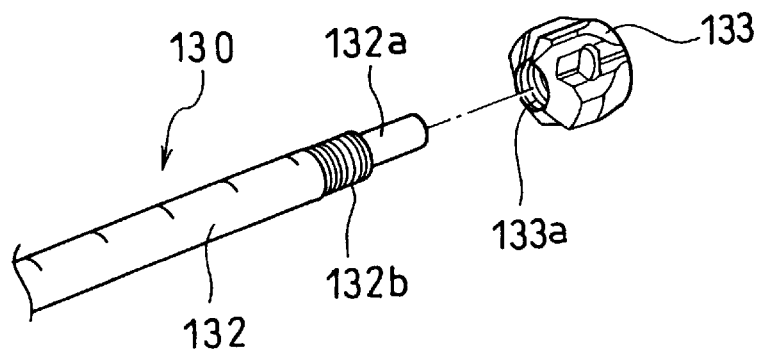
FIG. 15 is a perspective view showing a front end portion of a excavating apparatus of pulling/rotating type according to another embodiment of the present invention.

The engaging mode of the drill and shaft is not limited to the above-described one. It is possible to adopt bone-excavating apparatus of any type, provided that a rotational force of a shaft is transmitted to a drill when the shaft is rotated clockwise or counterclockwise so that the drill can excavate the bone and moreover, the drill is not removed from the shaft easily when the shaft is pulled toward the operator. For example, it is possible to adopt a bone-excavating apparatus 130 shown in FIG. 15. The construction of the bone-excavating apparatus 130 will be described below with reference to FIGS. 15, 16, and 17.

Similarly to the bone-excavating apparatus of the above-described embodiment, the bone-excavating apparatus 130 comprises a shaft 132 and a drill 133. The shaft 132 comprises a drill-guiding projection 132*a* and a male screw 132*b*. The drill-guiding projection 132*a* has a small diameter and is positioned at the front end of the shaft 132. The male screw 132*b* is located adjacently to the drill-guiding projection 132*a* and forms a shaft-side engaging portion. The drill 133 has a through-hole, the entire inner surface of which is cylindrical and has a female screw 133*a* forming a drill-side engaging portion. In order to install the shaft 132 on the drill 133, the shaft 132 is rotated in a direction, for example, clockwise in which the drill 133 is capable of excavating the bone until the engagement between the female screw 133*a* of the drill 133 and the male screw 132*b* of the shaft 132 is completed, i.e., until the rear end of the female screw 133*a* of the drill 133 reaches the rear (base side) end of the male screw 132*b* of the shaft 132. When the shaft 132 is rotated further clockwise, the rotational force of the shaft 132 is transmitted to the drill 133. As a result, the drill 133 rotates with the shaft 132, When the shaft 132 is rotated in a direction, for example, counterclockwise in which the drill 133 is incapable of excavating the bone, the male screw 132*b* disengages from the female screw 133*a*, and thus the shaft 132 and the drill 133 are removed from each other. It is preferable that the shape of the drill is identical to that of the drill 133.

Figure 16:
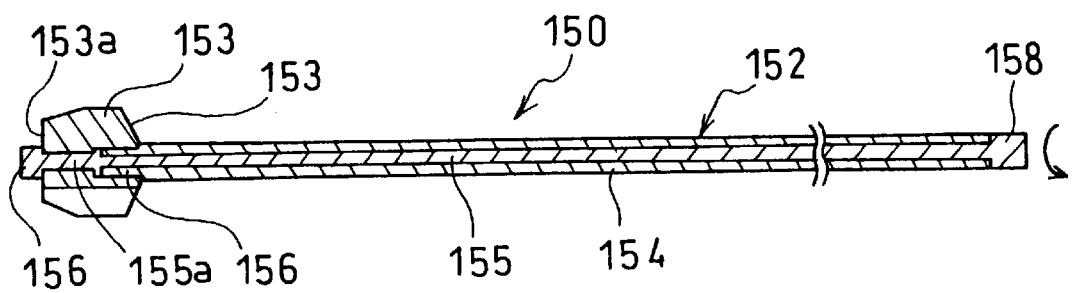
FIG. 16 is a partly abbreviated sectional view showing the bone-excavating apparatus shown in FIG. 15.
Figure 17:
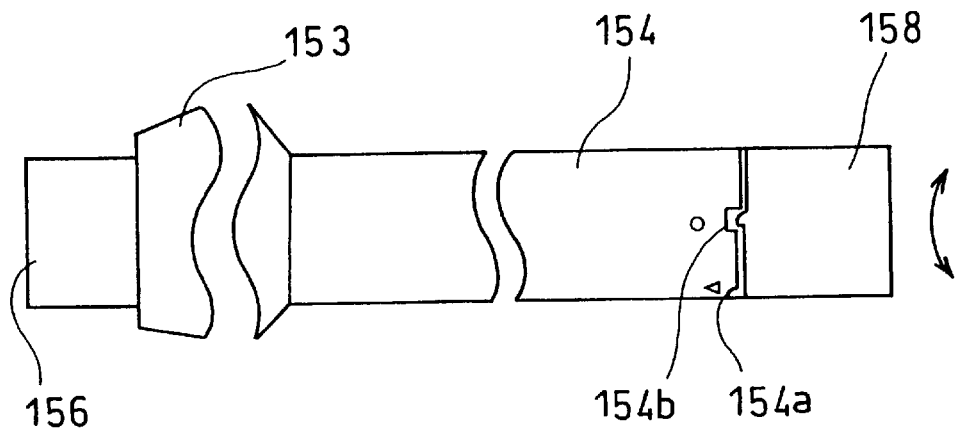
FIG. 17 is an enlarged plan view showing the front part and rear part of the bone-excavating apparatus shown in FIG. 16.

The apparatus 150 of pulling/rotating type shown FIGS. 16 and 17 may be used to repair the ligament. The apparatus 150 also comprises a shaft 152 and a drill 153.

The shaft 152 comprises a cylindrical sleeve 154 and a shaft member 155 which penetrates through the sleeve 154 and rotatable relative thereto. The shaft member 155 is inserted into the drill 153 from its front part. The front end 156 of the shaft member 155 has a flat portion consisting of two flat surfaces formed on a cylinder and extending in substantially parallel with each other in the axial direction of the shaft member 155. The shape of the through-hole of the drill 153 at its front surface 153*a* (blade-unprovided side) is oval, similarly to that of the flat portion of the shaft member 155. That is, the front surface 153*a* has a flat portion consisting of two flat parallel surfaces and circular arcs each continuous with the flat parallel surfaces. When the shaft member 155 is rotated, with the front end 156 of the shaft member 155 in penetration through the through-hole of the drill 153, a part of the edge of the front end 156 (flat portion) at the rear side thereof contacts the front surface 153*a* of the drill 153. When the shaft 152 is pulled rearward (toward the operator), the shaft 152 engages the drill 153. Thus, the shaft 152 can be prevented from being removed from the drill 153, and the pulling force applied to the shaft 152 is transmitted to the drill 153.

The shaft member 155 has a small-diameter portion 155*a* sectionally circular and continuous with the front end 156 (flat portion) thereof and a sleeve-locking portion 155*b* consisting of a rib so sized as not to interfere with the shaft member 155 when it rotates. The shaft member 155 further comprises a small-diameter portion sectionally circular and continuous with the sleeve-locking portion 155*b*, thus extending to the rear end thereof The shaft member 155 further comprises an operation portion 158 as shown in FIG. 17. The shaft member 155 is rotatable by about 90° relative to the sleeve 154 by rotating the operation portion 158. The operation portion 158 has a rib 158*a* confronting the rear end of the sleeve 154. The sleeve 154 has a first concave 154*a* and a second concave 154*b* at its rear end. When the rib 158*a* has engaged the first concave 154*a*, the flat surface of the front end 156 (flat portion) of the shaft member 155 is parallel (same phase) with the flat surface of the sleeve 154. When the rib 158*a* has engaged the second concave 154*b*, the flat surface of the front end 156 (flat portion) of the shaft member 155 is perpendicular (phases are different from each other by 90°) to the flat surface of the sleeve 154. With the rib 158*a* in engagement with the first concave 154*a*, the front part of the shaft 152 is inserted through the through-hole of the drill 153 from the blade-provided side thereof to project the front end 156 (flat portion) of the shaft member 155 from the front end of the drill 153. Then, the operation portion 158 is rotated to engage the rib 158*a* with the second concave 154*b* of the sleeve 154. As a result, a part of the edge of the front end 156 (flat portion) at the rear side thereof becomes coincident with the front surface 153*a* of the drill 153, with the front end 156 in contact with the front surface 153*a*. When the shaft 152 is pulled rearward (toward the operator), the shaft 152 engages the drill 153. Thus, the shaft 152 can be prevented from being removed from the drill 153.

The front end of the sleeve 154 has a flat portion (sectionally oval) consisting of two flat surfaces formed on a cylinder and extending in substantially parallel with each other in the axial direction of the shaft 152. The shape of the rear end of the through-hole of the drill 153 is sectionally oval, similarly to that of the flat portion of the sleeve 154. Therefore, when the sleeve 154 is rotated, one of the flat surfaces of the sleeve 154 contacts the flat surface of the through-hole of the drill 153. As a result, the rotational force of the sleeve 154 is transmitted to the drill 153, thus rotating the drill 153 with the shaft 152.

As apparent from the foregoing description, the bone can be excavated by pulling and rotating the shaft 152 (sleeve 154) clockwise. Drill having the shape of the drill 153 can be preferably used.

The bone-excavating apparatus 150 of pushing/rotating type which is used to repair the ligament will be described below with reference to the drawings.

Figure 18:
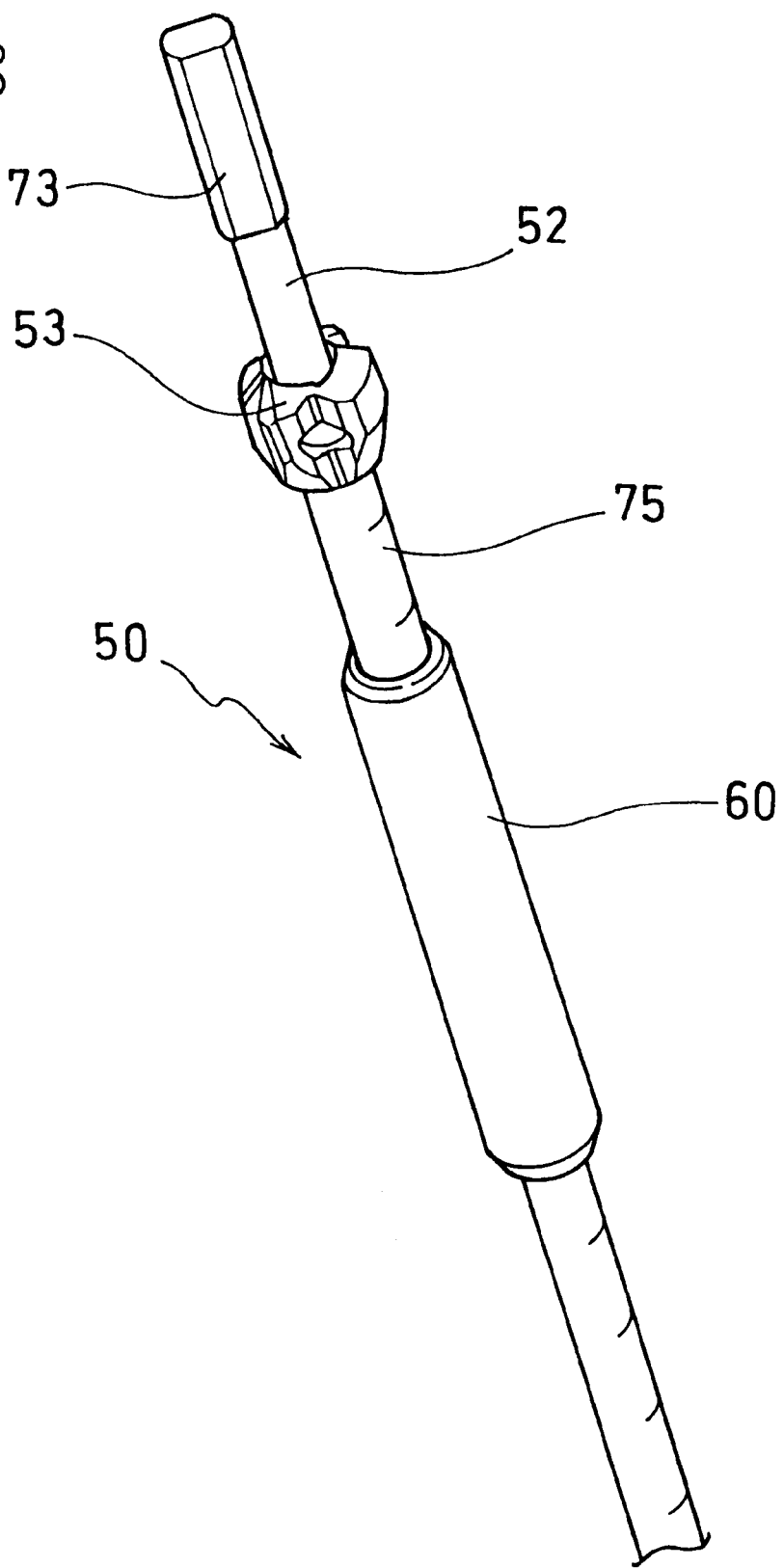
FIG. 18 is a perspective view showing the front part of a excavating apparatus of pushing/rotating type according to an embodiment of the present invention.
Figure 19:
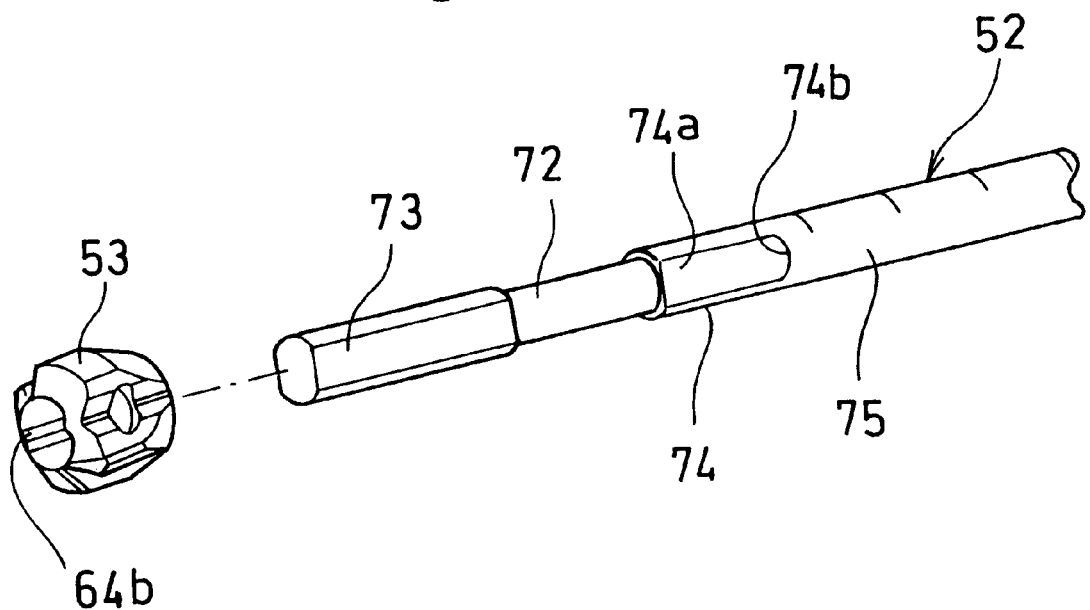
FIG. 19 is a perspective view showing a state in which a drill of the bone-excavating apparatus has been removed from a shaft thereof shown in FIG. 18.
Figure 20:
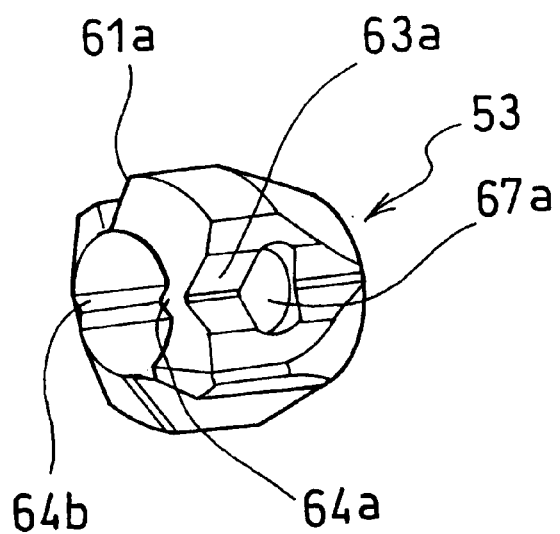
FIG. 20 is an enlarged perspective view showing the drill of the bone-excavating apparatus shown in FIG. 18.
Figure 21:
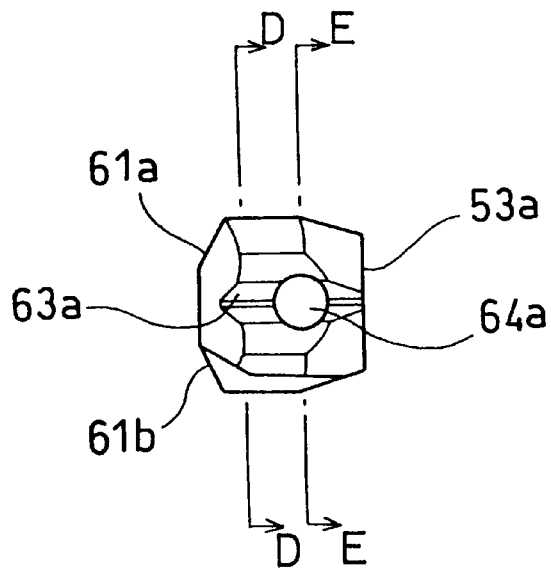
FIG. 21 is an enlarged front view showing the drill of the bone-excavating apparatus shown in FIG. 20.
Figure 22:
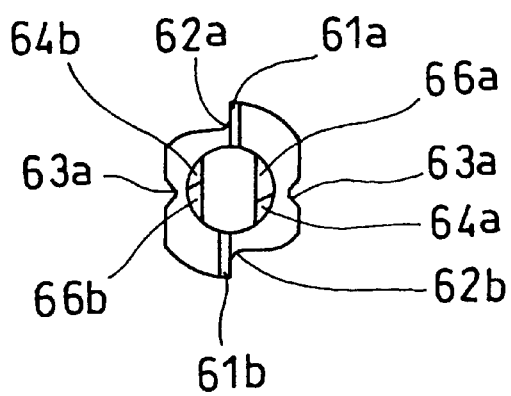
FIG. 22 is a left side elevation (side elevation of blade-provided side) showing the drill of the bone-excavating apparatus shown in FIG. 20.
Figure 23:
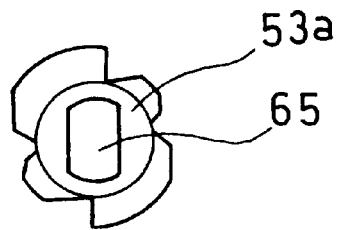
FIG. 23 is a right side elevation (side elevation of blade-unprovided side) showing the drill of the bone-excavating apparatus shown in FIG. 21.
Figure 24:
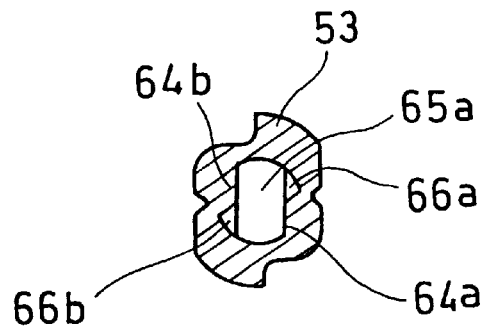
FIG. 24 is a sectional view taken along a line D—D of FIG. 21.
Figure 25:
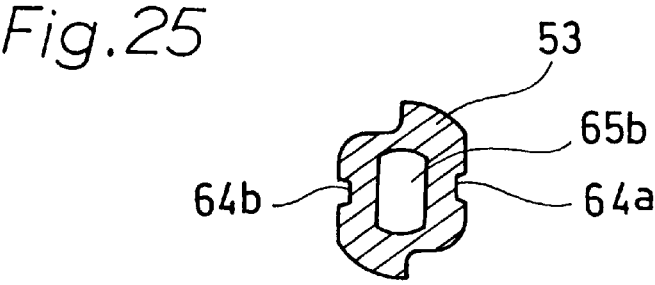
FIG. 25 is a sectional view taken along a line E—E of FIG. 21.

FIG. 18 is a perspective view showing the front part of a bone-excavating apparatus of pushing/rotating type according to an embodiment of the present invention. FIG. 19 is a perspective view showing a state in which a drill of the bone-excavating apparatus has been removed from a shaft thereof shown in FIG. 18. FIG. 20 is an enlarged perspective view showing the drill of the bone-excavating apparatus shown in FIG. 18. FIG. 21 is an enlarged front view showing the drill of the bone-excavating apparatus shown in FIG. 20. FIG. 22 is a left side elevation (side elevation of blade-provided side) showing the drill of the bone-excavating apparatus shown in FIG. 20. FIG. 23 is a right side elevation (side elevation of blade-unprovided side) showing the drill of the bone-excavating apparatus shown in FIG. 21. FIG. 24 is a sectional view (section at blade-provided portion and passage at this portion is in the shape of deformed gourd) taken along a line D—D of FIG. 21. FIG. 25 is a sectional view (passage at this portion is oval) taken along a line E—E of FIG. 21.

As shown in FIGS. 18 and 19, the bone-excavating apparatus 1 comprises a shaft 52 and a drill 53 (pushing/rotating drill) installably on and removably from the shaft 52 at its front end.

The drill 53 is hollow. The shaft 52 is rotated clockwise while it is being pushed toward its base side to form a bone tunnel, with the drill 53 inserted into the shaft 52. The drill 53 is so sized as to be inserted into the articulation from a skin-cutting portion thereof. It is preferable to set the outer diameter of the drill 53 and the length thereof to 7–12 mm, respectively.

Referring to FIGS. 20, 21, and 22, the drill 53 comprises blades 61a and 61b formed on only the rear end surface thereof to prevent the skin and a normal part of the ligament from being injured; cut dust discharging grooves 62a and 62b continuous with each of the blades 61a and 61b and extending axially on the lateral thereof. The drill 53 has two V-shaped holding grooves 63 (63a and 63b) formed on the lateral thereof and facing each other to prevent the drill 53 from being shaken by a gripping means such as a forceps when it is inserted into the articulation. The V-shaped holding grooves 63a and 63b extend axially and are parallel with each other. The drill 53 has concavities 67a and 67b formed on a lateral thereof. These concavities 67a and 67b are formed each of the V-shaped holding grooves 63a and 63b to prevent the drill 53 from dropping from the gripping means such as the forceps.

The front peripheral part of the drill 53 is tapered to form a tapered portion thereon so that the drill 53 can be inserted easily into the articulation. The corner at which the tapered portion and the front part of the drill 53 intersect with each other is rounded to prevent the corner from being brought into contact with the skin or the like.

As shown in FIG. 22, a shaft-inserting through-hole 65 is axially formed inside the drill 53. The through-hole 65 of the drill 53 comprises parts 65a and 65b. The part 65a is positioned rearward from the front end of the drill 53 thereof to about ½ of the whole length of the drill 53, as shown in FIG. 24 which is a sectional view taken along a line D—D in FIG. 21. The part 65a has projections 64a and 64b which are parallel with each other and formed on a part of its cylindrical inner surface, i.e., the inner surface of the part 65a is a deformed-gourd shaped sectionally. More specifically, the shape of the part 65a is formed by superimposing two similar or congruent quadrilaterals each having two parallel lines and two circular arcs on each other, with one quadrilateral rotated a predetermined angle (for example, 30–90°, 45° in the embodiment) on its center with respect to the other, after the centers of both quadrilaterals coincident with each other. The inner surface of the parallel projection 64a and that of the projection 64b project inward in confrontation with each other in the through-hole 65, thus forming a small flat surface, respectively extending in parallel with each other in the axial direction of the drill 53. As shown in FIG. 25 which is a sectional view taken along a line E—E in FIG. 21, the part 65b is positioned rearward from the part 65a to ½ of the whole length of the drill 53. The part 65b comprises two flat surfaces confronting each other and curved surfaces each continuous therewith. The two confronting flat surfaces are substantially parallel with each other and extend in the axial direction of the drill 53.

As shown in FIG. 23, a part of the through-hole 65 positioned at the rear end surface (blade-unprovided side) of the drill 53 is oval. That is, two parallel flat surfaces and circular arcs each continuous therewith are formed on the through-hole 65 at its rear end. A flat surface 53a is formed on the rear periphery of the opening of the through-hole 65. The flat surface 53a corresponds to a stepped portion 74b formed at the rear end of a second flat portion 74 of the shaft 52. The second flat portion 74 will be described later.

Referring to FIG. 19, the front end part of the shaft 52 comprises a first flat portion 73 constituting the insertion portion thereof into the drill 53 and the guide portion for guiding the drill 53 to the bone hole. Thus, it is preferable that the length of the first flat portion 73 is 20–30 mm. The first flat portion 73 has two flat surfaces 73a extending substantially parallel with each other in the axial direction of the shaft 52. The shaft 52 further comprises a small-diameter portion 72 positioned rearward from the first flat portion 73 and continuous therewith. The small-diameter portion 72 is longer than the entire length of the drill 53 and capable of holding the drill 53 thereon. The outer diameter or the maximum diameter of the small-diameter portion 72 is smaller than the shortest distance of the inner diameter of the part 65b, of the drill 53, the inner surface of which is oval sectionally. Therefore, the drill 53 rotates without contacting the small-diameter portion 72. The shaft 52 comprises the second flat portion 74 continuous with the small-diameter portion 72 and having two flat surfaces 74a extending in substantially parallel with each other in the axial direction of the shaft 52. The shaft 52 further comprises a cylindrical portion 75 continuous with the second flat portion 74. It is preferable that the outer diameter of the shaft 52 is 2–7 mm.

When the front end part of the shaft 52 is inserted into the through-hole 65 of the drill 53, the first flat portion 73, the small-diameter portion 72, and the second flat portion 74 penetrate through the through-hole 65, and the flat surface 53a formed on the rear end of the drill 53 contacts the stepped portion 74b formed at the rear end of the second flat portion 74 of the shaft 52. Thus, the drill 53 is prevented from moving toward the base (rear) side of the shaft 52 beyond the stepped portion 74b.

In this state, the front end of the small-diameter portion 72 of the shaft 52 is positioned within the front end part of the through-hole 65 of the drill 53. The second flat portion 74 of the shaft 52 is positioned within the part 65a whose inner surface is sectionally deformed gourd-shaped and the part 65b whose inner surface is sectionally oval. When the shaft 52 is rotated, the flat surface (drill side engaging portion) of the part 65b whose inner surface is sectionally oval and the flat surface 74a (shaft side engaging portion) of the second flat portion 74 of the shaft 52 engage each other. Therefore, the rotational force of the shaft 52 is transmitted to the drill 53, thus rotating the drill 53.

Figure 26:
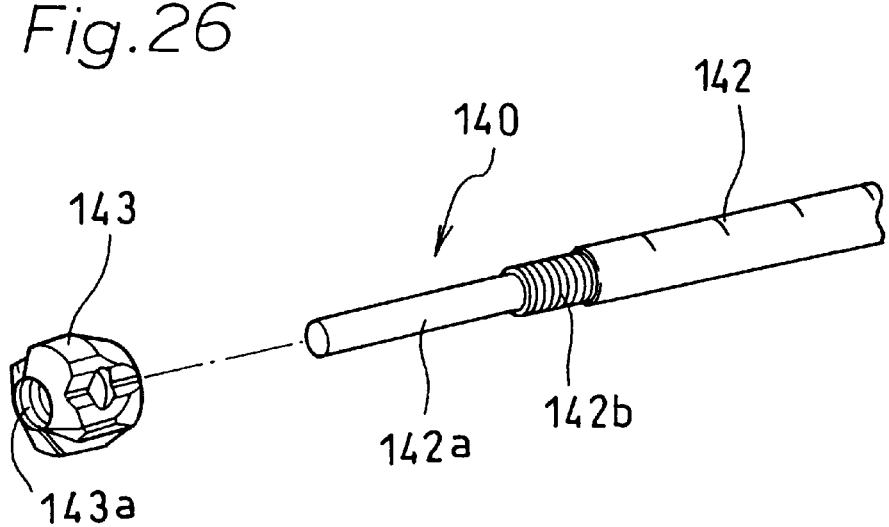
FIG. 26 is a perspective view showing the front part of a bone-excavating apparatus of pushing/rotating type according to another embodiment of the present invention.

When the shaft 52 is pulled, with the drill 53 installed thereon, the shaft 52 moves relative to the drill 53. If the drill 53 or the shaft 52 rotates slightly, with the drill 53 positioned on the small-diameter portion 72 of the shaft 72, the flat surface 73a of the first flat portion 73 of the shaft 52 contacts the flat parallel surface of the projections 64a and 64b formed on the inner surface of the part 65a of the through-hole of the drill 53 or the flat parallel surface of the part 65b of the through-hole of the drill 53. Consequently, the drill 53 is prevented from being removed from the shaft 52. That is, these members constitute a removal prevention mechanism. Thus, when the shaft 52 is pulled toward the operator during operation, the removal prevention mechanism prevents the shaft 52 from being removed from the bone hole. The removal prevention mechanism is not essential. The engaging mode of the drill and shaft is not limited to the above-described one. It is possible to adopt bone-excavating apparatus of any type, provided that a rotational force of a shaft is transmitted to a drill when the shaft is rotated clockwise or counterclockwise and moreover, the drill is not removed from the shaft easily when the shaft is pulled toward the operator. For example, it is possible to adopt a bone-excavating apparatus 140 shown in FIG. 26. The construction of the bone-excavating apparatus 140 will be described below with reference to FIG. 16.

Similarly to the bone-excavating apparatus of the above-described embodiment, the bone-excavating apparatus 140 comprises a shaft 142 and a drill 143. The shaft 142 comprises a drill-guiding projection 142a and a male screw 142b. The drill-guiding projection 142a has a small diameter and is positioned at the front end of the shaft 142. The male screw 142b is located adjacently to the drill-guiding projection 142a and forms a shaft-side engaging portion. The drill 143 has a through-hole, the entire inner surface of which is cylindrical and has a female screw 143a forming a drill-side engaging portion. In order to install the shaft 142 on the drill 143, the shaft 142 is rotated in a direction, for example, clockwise in which the drill 143 is capable of excavating the bone until the engagement between the female screw 143a of the drill 143 and the male screw 142b of the shaft 142 is completed, i.e., until the rear end of the female screw 143a of the drill 143 reaches the rear (base side) end of the male screw 142b of the shaft 142. When the shaft 142 is rotated further clockwise, the rotational force of the shaft 142 is transmitted to the drill 143. As a result, the drill 143 rotates with the shaft 142. When the shaft 142 is rotated in a direction, for example, counterclockwise in which the drill 143 is incapable of excavating the bone, the male screw 142b disengages from the female screw 143a, and thus the shaft 142 and the drill 143 are removed from each other. It is preferable that the shape of the drill is identical to that of the drill 143.

It is possible to use the apparatus of pushing/rotating type shown FIGS. 16 and 17 in which the shaft comprises the sleeve and the rotatable shaft member which is inserted into the sleeve.

According to the bone-excavating apparatus of the present invention, it is easy to form the bone tunnel allowing the excavation amount of bone and the number of bone-removed portions to be small and allowing the ligament to be repaired by taking out a small amount of normal part therefrom. More specifically, only a necessary amount of bone is excavated to form the bone tunnel when the articulation is not cut but the bone tunnel is formed backward. This method reduces the amount of bone to about as small as ⅓ or less of the amount which is excavated by the conventional method. In the case of an autotransplantation, the length of the ligament which is taken out is as small as 5–6 cm which is about ⅓–¼ of the length which is taken out by the conventional method.

While the present invention has been described with reference to preferred embodiments thereof, it is to be understood that the invention is not limited to the disclosed embodiments or constructions. On the contrary, the invention is intended to cover various modifications and equivalent arrangements included within the spirit and scope of the appended claims.

What is claimed is:

1. A bone-excavating apparatus for repairing a ligament, comprising:

a rod-shaped shaft;

a drill having a bone-excavating blade formed thereon such that the drill is insertable into an articulation from a cut portion thereof and installable on the shaft and removable from the shaft, wherein the drill and shaft on which the drill has been installed constitute a drill-locking mechanism for preventing the drill from being moved to a base side of the shaft;

a torque transmission mechanism for transmitting, to the drill, a rotational force applied to the shaft in a direction in which a bone-excavating blade is allowed to excavate the bone; and a shaft removal prevention mechanism for allowing an engagement of the shaft with the drill when the shaft is pulled toward the base side thereof;

wherein said drill has two grooves provided to the lateral thereof and extending axially and facing each other and concavities provided to the lateral thereof and facing each other and formed on each of the grooves.

2. The bone-excavating apparatus according to claim 1, wherein the shaft removal prevention mechanism comprises a drill side engaging portion and a shaft side engaging portion both engaging each other when the shaft on which the drill has been installed is rotated in a direction in which the bone-excavating blade is allowed to excavate the bone and both disengaging from each other when the shaft is rotated in a direction in which the bone-excavating blade is not allowed to excavate the bone.

3. The bone excavating apparatus according to claim 1, wherein the drill has a through-hole into which a front part of the shaft is inserted; and a projection extending axially formed on an inner surface of the through-hole; an opening of the through-hole at an end part of the drill is formed of parallel lines and circular arcs continuous with the parallel lines, a front part of the shaft constituting an insertion part thereof into the drill comprises a flat portion which has two flat surfaces formed on a cylinder and extending in substantially parallel with each other in an axial direction of the shaft and which projects from the through-hole of the drill when the drill is installed on the shaft; and a small-diameter portion continuous with the flat portion and formed at a side rearward therefrom, when a rotational force is applied to the shaft in a direction in which a bone-excavating blade is allowed to excavate the bone, with the front part of the shaft inserted into the through-hole of the drill, the shaft is rotatable slightly with respect to the drill, and the shaft removal prevention mechanism comprises the end part of the drill and a portion, of a rear side edge of the flat portion projecting from the drill, which is coincident and contacts the end part of the drill when the shaft is rotated slightly with respect to the drill.

4. The bone-excavating apparatus according to claim 1, wherein the shaft comprises a flat surface extending axially, the drill has a through-hole insertable into the flat surface of the shaft; and a projection formed on an inner surface of the through-hole and extending axially, the projection and the flat surface constitute a torque transmission mechanism, and the projection of the drill installed on the shaft and the flat surface of the shaft contact each other when a rotational force is applied to the shaft in a direction in which the bone-excavating blade is allowed to excavate the bone.

5. The bone-excavating apparatus according to claim 1, wherein the drill has a through-hole into which a front part of the shaft is inserted; and a projection extending axially formed on an inner surface of the through-hole, a front part of the shaft constituting an insertion part thereof into the drill comprises a flat portion having two flat surfaces formed on a cylinder and extending in substantially parallel with each other in an axial direction of the shaft; and a cylindrical portion continuous with the flat portion and formed at a side rearward therefrom, a drill-locking mechanism for preventing the drill from being moved to the base side of the shaft comprises a blade-provided side end of the projection of the drill; and a front side end of the cylindrical portion of the shaft which contacts the blade-provided side end of the projection when the front part of the shaft is inserted into the through-hole of the drill.

6. The bone-excavating apparatus according to claim 1, wherein the drill has two blades formed on only a rear surface thereof and two cut dust-discharging grooves continuous with the blades and extending axially on a lateral thereof.

7. The bone-excavating apparatus according to claim 1, wherein the drill has two blades formed on only a front surface thereof and two cut dust-discharging grooves continuous with the blades and extending axially on a lateral thereof.

8. A bone-excavating apparatus for repairing a ligament, comprising a rod-shaped shaft; and a drill having bone-excavating blade formed thereon such that the drill is insertable into an articulation from a cut portion thereof and installably to the shaft and removably from the shaft, wherein the drill has a through-hole into which a front part of the shaft is inserted; and a projection extending axially formed on an inner surface of the through-hole; an opening of the through-hole at an end part of the drill is formed of parallel lines and circular arcs continuous with the parallel lines, a front part of the shaft constituting an insertion part thereof into the drill comprises a first flat portion having two flat surfaces formed on a cylinder and extending in substantially parallel with each other in an axial direction of the shaft; a small-diameter portion continuous with the first flat portion and formed at a side rearward therefrom; a second flat portion continuous with the small-diameter portion and having two flat surfaces formed on a cylinder and extending in substantially parallel with each other in the axial direction of the shaft; and a cylindrical portion continuous with the second flat portion, when the front part of the shaft is inserted into the through-hole of the drill, a blade-provided side end of the projection of the drill contacts an end of the cylindrical portion, thus preventing the drill from moving toward a base side of the shaft;

when a rotational force is applied to the shaft in a direction in which the bone-excavating blade is allowed to excavate the bone, the shaft rotates slightly relative to the drill; one of the flat surfaces of the second flat portion contacts one of the surfaces of the projection formed in the through-hole of the drill, thus transmitting the rotational force of the shaft to the drill; a slight amount of the rotation of the shaft relative to the drill causes a part of a rear side edge of the first flat portion to be coincident and contact an end surface of the drill; and when the shaft is pulled toward the base side thereof, the edge of the first flat portion and the end of the drill engage each other.

9. A bone tunnel forming method for a ligament-repairing operation comprising the steps of:

forming a small bone hole extending from a tibia to a femur;

forming a skin-cut portion at an articulation;

inserting a drill of a bone-excavating apparatus into the articulation from the skin-cut portion;

inserting a front end of a shaft of the bone-excavating apparatus into the articulation from an opening of the bone hole positioned at the tibia side;

installing the drill on the front end of the shaft in such a manner that a blade of the drill faces a rear side of the shaft;

rotating and pulling the shaft to excavate the bone by the drill and forming a bone tunnel of 10%–50% of the length of the small bone hole of the tibia;

removing the shaft from the drill;

taking out the drill from the articulation and drawing out the shaft from the small bone hole.

10. A bone tunnel forming method of the claim 9 further comprising the steps of:

inserting a drill of a bone-excavating apparatus into the articulation from the skin-cut portion;

inserting a front end of a shaft of the bone-excavating apparatus into the articulation from the skin-cut portion;

inserting a front end of a shaft of the bone-excavating apparatus into the articulation from an opening of the bond hole positioned at the tibia side;

installing the drill on the front end of the shaft in such a manner that a blade of the drill faces a front side of the shaft;

rotating and pushing the shaft to excavate the bone by the drill and forming a bone tunnel of 10%–50% of the length of the small bone hole of the femur;

removing the shaft from the drill;

taking out the drill from the articulation and drawing out the shaft from the small bone hole.

11. A bone tunnel forming method of the claim 9 further comprising the steps of:

inserting a drill of a bone-excavating apparatus into the articulation from the skin-cut portion;

inserting a front end of a shaft of the bone-excavating apparatus into the articulation from an opening of the bone hole positioned at the femur side;

installing the drill on the front end of the shaft in such a manner that a blade of the drill faces a rear side of the shaft;

rotating and pulling the shaft to excavate the bone by the drill and forming a bone tunnel of 10%–50% of the length of the small bone hole of the femur;

removing the shaft from the drill;

taking out the drill from the articulation and drawing out the shaft from the small bone hole.

12. A bone tunnel forming method for a ligament-repairing operation comprising the steps of:

forming a small bone hole extending from a tibia to a femur;

forming a skin-cut portion at an articulation;

inserting a drill of a bone-excavating apparatus into the articulation from the skin-cut portion;

inserting a front end of a shaft of the bone-excavating apparatus into the articulation from an opening of the bone hole positioned at the femur side;

installing the drill on the front end of the shaft in such a manner that a blade of the drill faces a front side of the shaft;

rotating and pushing the shaft to excavate the bone by the drill and forming a bone tunnel 10%–50% of the length of the small bone hole of the tibia;

removing the shaft from the drill;

taking out the drill from the articulation and drawing out the shaft from the small bone hole.

13. A bone tunnel forming method of the claim 12 further comprising the steps of:

inserting a drill of a bone-excavating apparatus into the articulation from the skin-cut portion;

inserting a front end of a shaft of the bone-excavating apparatus into the articulation from an opening of the bone hole positioned at the tibia side;

installing the drill on the front end of the shaft in such a manner that a blade of the drill faces a front side of the shaft;

rotating and pushing the shaft to excavate the bone by the drill and forming a bone tunnel of 10%–50% of the length of the small bone hole of the femur;

removing the shaft from the drill;

taking out the drill from the articulation and drawing out the shaft from the small bone hole.

14. A bone tunnel forming method of the claim 12 further comprising the steps of:

inserting a drill of a bone-excavating apparatus into the articulation from the skin-cut portion;

inserting a front end of a shaft of the bone-excavating apparatus into the articulation from an opening of the bone hole positioned at the femur side;

installing the drill on the front end of the shaft in such a manner that a blade of the drill faces a rear side of the shaft;

rotating and pulling the shaft to excavate the bone by the drill and forming a bone tunnel of 10%–50% of the length of the small bone hole of the femur;

removing the shaft from the drill;

taking out the drill form the articulation and drawing out the shaft from the small bone hole.

* * * * *